United States Patent [19]

Hirose

[11] Patent Number: 5,180,244
[45] Date of Patent: Jan. 19, 1993

[54] VISCOUS LIQUID APPLICATOR

[75] Inventor: Kazunori Hirose, Yamanashi, Japan

[73] Assignee: Terumo Kabushiki Kaisha, Tokyo, Japan

[21] Appl. No.: 757,895

[22] Filed: Sep. 11, 1991

[30] Foreign Application Priority Data

Sep. 14, 1990 [JP] Japan .................. 2-244267

[51] Int. Cl.$^5$ ............................................ A45D 34/00
[52] U.S. Cl. .................................. 401/264; 401/132; 401/262
[58] Field of Search ............... 401/132, 206, 264, 262, 401/263

[56] References Cited

U.S. PATENT DOCUMENTS

| 743,430 | 11/1903 | Berg | 401/264 |
|---|---|---|---|
| 1,006,075 | 10/1911 | Foster | 401/264 X |
| 1,608,570 | 11/1926 | Tuggle | 401/264 |
| 2,706,580 | 4/1955 | Keith | 401/264 X |
| 4,480,940 | 11/1984 | Woodruff . | |

FOREIGN PATENT DOCUMENTS

| 0390922 | 10/1990 | European Pat. Off. . | |
|---|---|---|---|
| 3020375 | 12/1981 | Fed. Rep. of Germany | 401/264 |
| 63-181776 | 7/1988 | Japan . | |
| 838800 | 6/1960 | United Kingdom . | |
| 8905695 | 6/1989 | World Int. Prop. O. | 401/206 |

Primary Examiner—Steven A. Bratlie
Attorney, Agent, or Firm—Frishauf, Holtz, Goodman & Woodward

[57] ABSTRACT

A viscous liquid applicator which comprises a cylindrical container containing a viscous liquid therein, and an applying member fitted in the distal end portion of the container in such a manner that it is capable of reciprocally moving in the axial direction of the container. A space is formed between the inner surface of the distal portion of the container and the outer surface of the applying member. The viscous liquid can be taken out of the container by pressing it to pass through the space, thus adhering the applying material on the outer surface of the applying member as the applying member is moved into the container. The applying member may be provided on its outer surface with a groove or grooves through which the applying material can be taken out of the container.

9 Claims, 4 Drawing Sheets

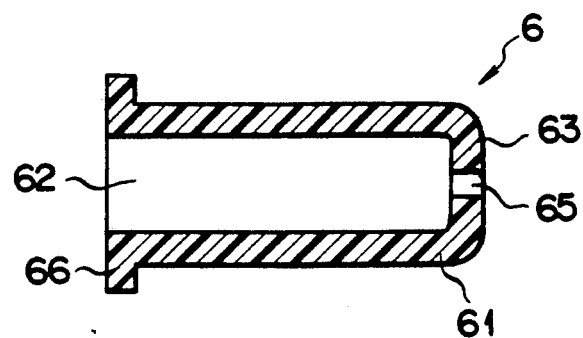
F I G. 3
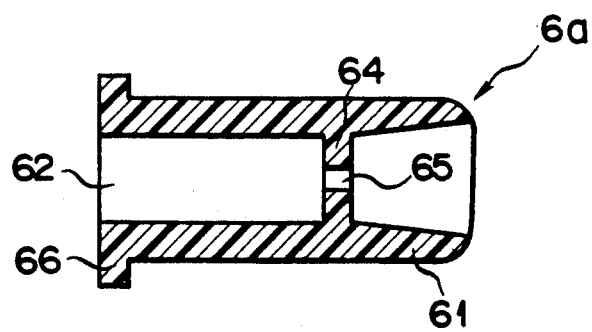
F I G. 4
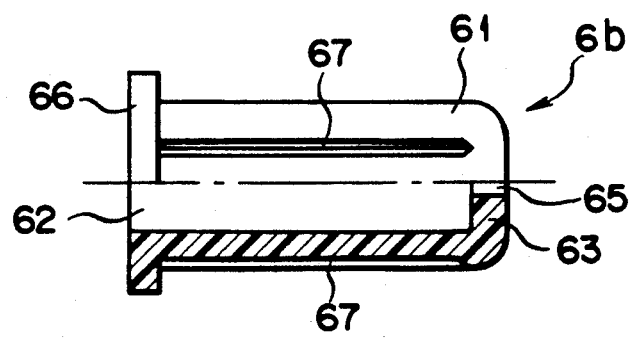
F I G. 5

VISCOUS LIQUID APPLICATOR

BACKGROUND OF THE INVENTION

1. Field of the Invention

This invention relates to a viscous liquid applicator for applying a viscous liquid such as an ointment or cream onto a portion of a living body.

2. Description of the Related Art

Liquid applicators are widely employed in various fields. In the medical industry, liquid applicators are employed for applying a medical liquid onto a diseased portion of a body.

Many types of applicators for medical purpose have been developed. For example, an applicator which is easy to handle and sanitarily safe has been recently developed as disclosed for example in Japanese Patent Unexamined Publication No. 63-181776 or PCT/JP88/01234.

These known applicators comprise a container which can be opened by being broken, and an applying member impregnated with a medical liquid. When this applicator is to be used, the container is first broken, thus forming an opening and thereby exposing a portion of the applying member. Thereafter, the exposed portion of the applying member is contacted with a diseased body portion to coat the medical liquid thereon.

In the treatment of, for example, dermatitis conditions such as pimples, a rash, and external wound, and an insect bite, a viscous liquid or semi-liquid such as an ointment or cream (hereinafter referred to as a viscous material) is often employed.

In the employment of such a viscous material, the viscous material is extruded by pressing a tubular container, and then the extruded material is coated onto the diseased part with the tip of a finger. However, when the viscous material is coated in this way, it will give rise to various problems such as unpleasant feelings due to the adhesion of the viscous material to the tip of the finger, the remainder of the viscous material being left on the tip of the finger, or due to the stickiness or bad smelling of the viscous material, difficulty in cleaning of the tip of the finger, or the contamination of the diseased portion through the germs which have been stuck on the tip of the finger. Accordingly, it is desirable to use a liquid applicator in the applying of such a viscous material as mentioned above.

However, the conventional liquid applicator is generally constructed for applying a liquid material which is relatively low in viscosity. Therefore, the applying member has been made from a material having minute pores for allowing the impregnation of the liquid therein, such as non-woven fabric, or a bundle of fibers. However, it is almost impossible for a viscous material to impregnate into such an applying member. Even if the viscous material can be impregnated into the applying member, it is difficult for a desired amount of the liquid to be extruded out of the applying member unless a high pressure is applied to the liquid due to the generation of a high fluid resistance within the applying member of the viscous liquid. Accordingly, it is almost impossible to use the conventional liquid applicator for a viscous liquid. Accordingly, there has been a demand for the development of a new liquid applicator which is suitable for applying a viscous liquid.

SUMMARY OF THE INVENTION

Therefore, one of the objects of this invention is to provide a viscous liquid applicator which is suited for applying a viscous liquid, easy to handle, and highly hygienic.

It has been found that above object can be attained by the present invention having the features as defined as follows.

(1) A viscous liquid applicator which comprises:
  a cylindrical container having a closed bottom, and comprising an applying material-filling portion and coater-supporting portion;
  an applying material comprising viscous liquid or semi-liquid filled in said applying material-filling portion; and
  an applying member fitted in said supporting portion so as to be movable in the axial direction of said cylindrical container;
  said applying member being provided with a passage which allows the applying material-filling portion to communicate with an exterior of said container.

(2) A viscous liquid applicator as described in (1) mentioned above, wherein the applying member is cylindrical in configuration, and comprises a barrier wall formed across an intermediate or end portion of the internal cavity of the applying member, and at least one through hole formed in the barrier wall.

(3) A viscous liquid applicator as described in (1) mentioned above, wherein said applying member is inserted in the cavity of the coater-supporting portion, and a fluid passage for the applying material is formed between the outer surface of the applying member and an inner surface of the coater-supporting portion.

(4) A viscous liquid applicator as described in (1) mentioned above, wherein an elastic member is disposed in said applying material-filling portion so as to energize said applying member to a direction opposite to said applying material-filling portion.

(5) A viscous liquid applicator as described in (1) mentioned above, which further comprises a cap covering at least a portion of said applying member, and connected via a thin portion to said coater-supporting portion;
  one end of said cap which is opposite to said thin portion being formed into a shape capable of capping said coatersupporting portion.

According to the viscous liquid applicator of this invention, when the applying member is pushed toward the applying material-filling portion while closing its passage thereby increasing the pressure within the applying material-filling portion, the viscous or semi-liquid applying material within the applying material-filling portion is extruded outward, or toward a fluid passage or groove formed between the outer surface of the applying member and the inner surface of the coater-supporting portion.

The applying material thus extruded passes through the fluid passage or the groove, and finally sticks on the side surface of the distal end portion of the applying member.

When the applying member is allowed to set back to the original position, the distal end portion of the applying member is extruded out of the supporting portion. Therefore the applying material stuck on this exposed portion of the applying member can be easily coated onto an object to be coated.

If a spring which is adapted to bias the applying member to move to a direction opposite to the applying material-filling portion is built in the container, the applying member can be automatically set back to the original position.

As the applying member returns to its original position, the external air is introduced through the passage formed in the applying member into the applying material-filling portion, thus restoring the original pressure within the applying material-filling portion to prepare for the next extrusion of the applying material by the movement of the applying member as mentioned above.

Additional objects and advantages of the invention will be set forth in the description which follows, and in part will be obvious from the description, or may be learned by practice of the invention. The objects and advantages of the invention may be realized and obtained by means of the instrumentalities and combinations particularly pointed out in the appended claims.

BRIEF DESCRIPTION OF THE DRAWINGS

The accompanying drawings, which are incorporated in and constitute a part of the specification, illustrate presently preferred embodiments of the invention, and together with the general description given above and the detailed description of the preferred embodiments given below, serve to explain the principles of the invention.

FIGS. 3, 4 and 5 respectively show another embodiment of the applying member according to this invention.

DETAILED DESCRIPTION OF THE PREFERRED EMBODIMENTS

Figure 1:
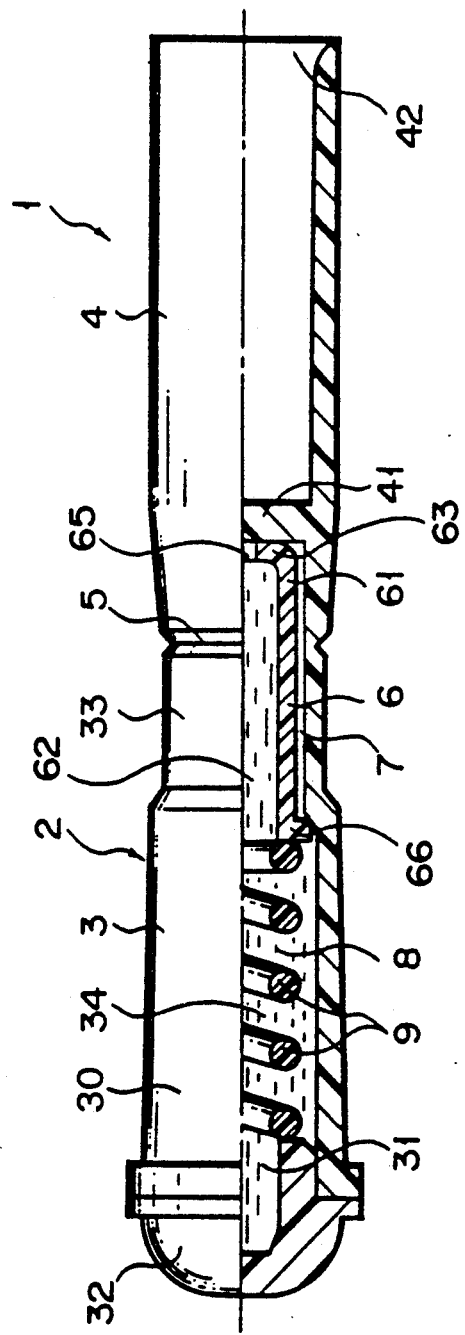
FIG. 1 is a sectional view of the viscous liquid applicator according to this invention.

This invention will be further explained with reference to the drawing depicting preferred embodiments.

FIG. 1 shows a vertical sectional view of a viscous liquid applicator of this invention. As shown in FIG. 1, the applicator 1 comprises a cylindrical container 2 having a closed bottom.

The container 2 is a hollow cylinder closed at one end, and comprises a main body 3 and a cap 4. The main body 3 supports the applying member 6. The cap 4 surrounds at least one portion of the applying member 6. The main body 3 and the cap 4 are connected together by a thin-walled portion 5 which can be broken by hand.

The main body 3 is cylindrical in configuration, and comprises an applying material-filling portion 30 at the proximal end side thereof, and a coater-supporting portion 33 at the distal end side thereof.

An opening 31 is formed at the proximal end of the applying material-filling portion 30, and a bottom cap 32 is inserted into this opening 31 for hermetically sealing the opening 31.

The coater-supporting portion 33 has a cavity therein, into which the applying member 6 is inserted and supported therein in such a manner that the applying member 6 is free to move (or slide) in the axial direction of the container 2.

The cap 4 is also cylindrical in configuration, and is provided with a barrier wall 41 extending traverse to its inner passage.

When the container 2 is in an unsealed state as shown in FIG. 1, the cap 4 covers the exposed portion 61 of the applying member 6.

Between the distal end of the main body 3 and the proximal end of the cap 4 is formed a thin-walled portion 5. In the embodiment shown in the FIG. 1, the thin-walled portion 5 is formed circumferentially around the container 2 in the form of a V-shaped groove.

When using the applicator 1, the thin-walled portion 5 is broken to separate the cap 4 from the main body 3.

It is preferable to dispose the thin-walled portion 5 at a position which corresponds to the outer circumference of the applying member 6 as will be explained below.

FIGS. 3 to 5 show sectional views of various examples of the applying member 6.

As shown in FIG. 3, the applying member 6 is cylindrical, having a circular cross-section and is provided at the distal end of its inner cavity 62 with a barrier wall 63, in which at least one through hole 65 is formed. The inner cavity 62 and through hole 65 provide a passage for communicating the interior of the applying material-filling portion 30 with the distal end of the applying member 6.

On the outer circumference of the proximal end of the applying member 6 is formed a circular rib 66 which is adapted to be engaged with the inner proximal end of the supporting portion 33. In other words, due to the presence of this rib 66, the applying member 6 is prevented from being detached from the main body 3.

In the case of an applying member 6a as shown in FIG. 4, the position of the barrier wall 64 relative to the applying member is somewhat changed. That is, in the case of applying member 6a, the barrier wall 64 is formed at an intermediate portion of the inner cavity 62. As in the case of the previous embodiment of FIG. 1, at least one through hole 65 is formed in the barrier wall 64.

Since the barrier wall 64 is located at an intermediate portion of the inner cavity 62 in the case of the applying member 6a, the distal end portion (an exposed portion 61 as explained hereinafter) of the applying member 6 can be made so as to be easily deformed Therefore, the applying material 8 can be easily applied to the skin of human body and the touching feeling of the applying member 6a to the skin is excellent.

The applying member 6b shown in FIG. 5 has almost the same construction as that of the applying member 6 shown in FIG. 3 except that a groove (or grooves) 67 extending in the axial direction of the applying member 6b is formed on the outer circumferential wall. This groove 67 constitutes a passage for allowing the applying material 8 within the applying material-filling portion 30 to extrude out of the applying material-filling portion 30.

The number of grooves 67 may be only one. However, it may be more preferable that a plurality of grooves 67 are formed on the applying member 6 as being suitably or equidistantly spaced apart from each other.

The shape or pattern of the groove (or grooves) 67 can be suitably selected. For example, the groove 67 may be formed helically on the outer surface of the applying member 6.

In the embodiments shown in FIGS. 3 to 5, only a single through hole 65 is formed in the barrier wall. However, a plurality of through holes 65 may be formed in the barrier wall 63 or 64.

The materials for the applying members 6, 6a and 6b should be preferably selected from those which are inert to the applying material 8. For example, polypropylene, polyethylene, polyvinyl chloride, polyethylene telephthalate, polystyrene,, polycarbonate, acrylic resin, ABS resin, silicone resin, thermoplastic elastomer, olefin copolymer, natural rubber, isoprene rubber, silicone rubber, styrene rubber, nitrile rubber, butyl rubber, glass, ceramics such as alumina and metals such as stainless steel or aluminum can be employed.

Among these, polypropylene, polyethylene, polyvinyl chloride and polystyrene are more preferable in view of ease of manufacturing and lowering of manufacturing cost.

When the feeling of the touch to the skin of the applying materials is taken as being important, the employment of elastic materials such as various types of rubber, silicone resin and thermoplastic elastomer are preferable.

As to the size of the applying members 6, 6a and 6b, there is no particular limitation. However, applying members having an outer diameter of 1 to 50 mm, more preferably 5 0 to 25 mm, an inner diameter of 0.5 to 49 mm, more preferably 4.0 to 24 mm, and a length (length in the axial direction of the container) of 5 to 30 mm, more preferably 10 to 30 mm may be generally employed.

The area of the opening of the through hole 65 should preferably be 0.5 to 10 mm$^2$, more preferably 0.5 to 1 mm$^2$.

The applying member 6, 6a and 6b (hereinafter simply referred to as the applying members 6) are disposed within the supporting portion 33. In this case, a space or clearance is formed between the outer surface of the applying member 6 and the inner surface of the supporting portion 33, thus forming a fluid passage 7 for the applying material 8. It is preferable that the distance or space between the outer surface of the applying member 6 and the inner surface of the supporting portion 33 (or a half of the difference in diameter between the inner diameter of the supporting portion 33 and the outer diameter of the applying member 6) be set to 2 mm or less, more preferably 0.5 to 1.5 mm.

When the applying member 6b of FIG. 5 is employed, the distance between the outer surface of the applying member 6b and the inner surface of the supporting portion 33 may be less than 0.5 mm, since the groove 67 functions as a passage for allowing the applying material 8 to pass therethrough.

Another groove (not shown) may be formed in the inner surface of the supporting portion 33 in the same manner as that of the groove 67, thereby obtaining almost the same effect as that of the groove 67.

Figure 2:
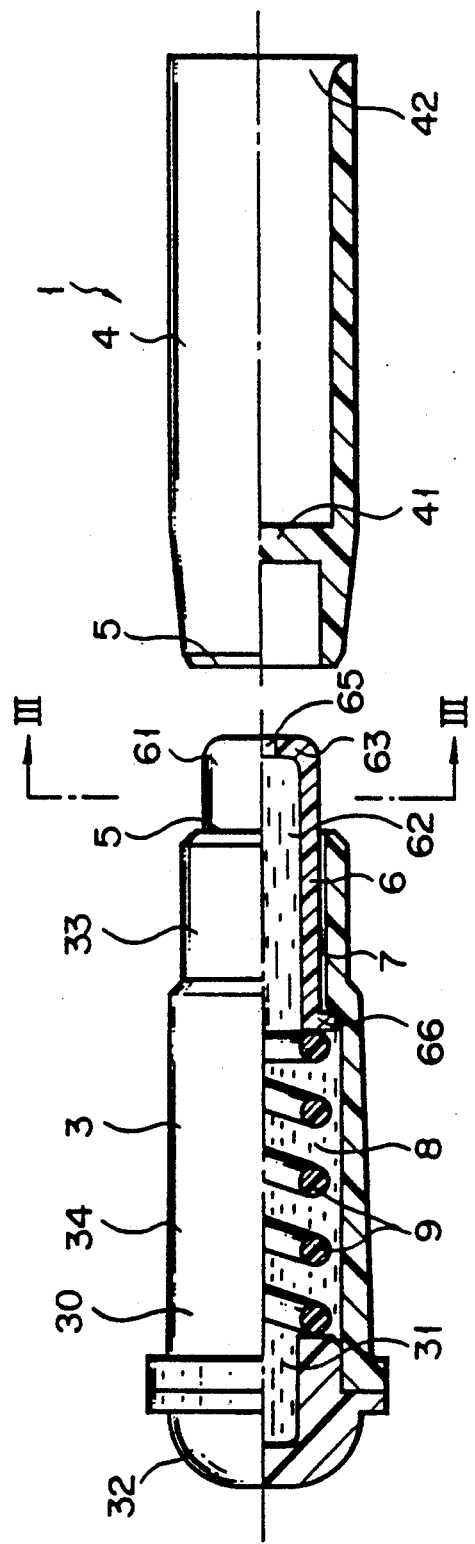
FIG. 2 is a sectional view of the viscous liquid applicator which has been unsealed.

The applying material 8 is filled in applying material-filling portion 30 of the main body 3 as shown in FIGS. 1 and 2. This applying material 8 is of relatively high viscosity or semi-liquid (fluid materials). Namely, the viscosity of the applying material 8 may preferably be 30 to 5000 cp, generally 1000 to 3500 cp at normal ambient temperature.

There is substantially no restriction as to the type of liquid 8 to be employed in this invention. Any of medical or non-medical materials can be employed. Among medical liquids which may be employed are: an ointment containing medicine, cream and lotion. Among non-medical liquids which may be employed are: cosmetics, such as manicure, skin cream, lotion, eyeliner, liquid or semi-liquid powder, perfume, milky lotion, pomade, stick pomade, hair lotion, and hair dye; liquids for use in offices, such as glue, adhesives, glue, correction liquid and water colors; foods or cooking materials such as bean paste, cooking oil lard, margarine, agar and gelatin; liquid for industrial use, such as lubricant, anticorrosives, wax, detergent, paint, glue, adhesives such as varnish, sealant and liquid resins.

The applying material 8 can be filled in the container 2 in any amount desired. Preferably, it is filled in an amount ranging from 0.2 to 5 ml, more preferably from 0.3 to 0.8 ml.

As is evident from in FIG. 1, it is desirable that the applying member 6, is biased toward the cap 4, by a resilient member. In this regard, a coil spring 9 is contacted or connected at its end to the inner surface of the bottom cap 32 and at the other end to the proximal end of the member 6. The distal end of the coil spring 9 is connected to the proximal end of the applying member 6. The coil spring 9 can be replaced by a leaf spring or any other resilient member.

Until the case 2 is broken at the thin wall portion 5 as shown in FIG. 1, the coil spring 9 is expanded or somewhat compressed, pushing (biasing) the applying member 6 toward the cap 4, with the rib 66 of the applying member 6 being engaged with the inner side of the proximal end of the supporting portion 33. When the container 2 is broken at the thin wall portion 5, for separating the main body 3 and the cap 4 from each other, the distal end portion 61 of the applying member 6 is exposed. Thereafter, the side surface 63 of the applying member 6 is placed in contact with the prescribed portion (hereinafter referred to as an applying portion) to be applied with the applying material, and then the applying material 8 is coated thereon.

When the applying material 8 is to be applied, the distal end surface 63 of the applying member 6 is contacted to the applying portion with the through hole 65 being sealed (in the case of the applying member 6a, the distal open end is sealed), and the exposed portion 61 is pressed toward the main body 3 against the elasticity of the spring 9. As a result, the spring 9 is compressed and the applying member 6 is shifted inward, thereby increasing the pressure within the applying material-filling portion 30 and causing the applying material 8 to be extruded through the passage or clearance 7 from the proximal end of the applying member 6 to the side surface 63 of the exposed portion 61. In the case of the applying member 6b of FIG. 5, the applying material 8 can be extruded through the groove 67 to the side surface 63 of the exposed portion 61.

When the applying member 6 is released form the pushing force, the coil spring 9 expands to its original length, thus moving the member 6 to the initial position. At this occasion, outside air is introduced into the applying material-filling portion 30 through the through hole 65 and the inner cavity 62, thereby restoring the pressure within the applying material-filling portion 30 to the original state, thus making it possible to allow another extrusion of the applying material 8.

The case 2 and the bottom cap 32 should preferably be made of material which is inert to the applying material 8 and which can form a gas barrier for preventing, to some extent, the applying material 8 from evaporating. They can be made of various resins including polypropylene, polyethylene, polyvinyl chloride, polyvinylidene chloride, polyethylene telephthalate, polystyrene, polycarbonate, acrylic resin, ABS resin, silicone resin. Alternatively, they can be made of various ceramics such as glass and alumina, or various metals such as stainless steel and aluminum. Of these materials, the most preferable are polypropylene, polyethylene, polyvinyl chloride, and polystyrene. This is because, the container 2, if made of one of these resins, can easily be broken at the thin wall portion 5, and the container 2 and the bottom cap 32, if made of one of these resins, can be easily manufactured at low cost.

The main body 2 and the cap 4 can be separately prepared and then connected together by fusing or bonding, thereby forming the integral container 2. To reduce the number of components of the applicator 1, however, it is preferable that the main body 3 and the cap 4 be formed integral, made of the same material or multi-color formed with different materials such as two colored formation.

The coil spring 9 should preferably be made of a material which is inert to the applying material 8. To be more specific, it is desirable that the spring 9 be made of various resins such as polypropylene, polyethylene, polyvinyl chloride, polyethylene telephthalate, polystyrene, polycarbonate, acrylic resin, ABS resin and silicone, or various metals such as stainless steel, aluminum and titanium.

Figure 6:
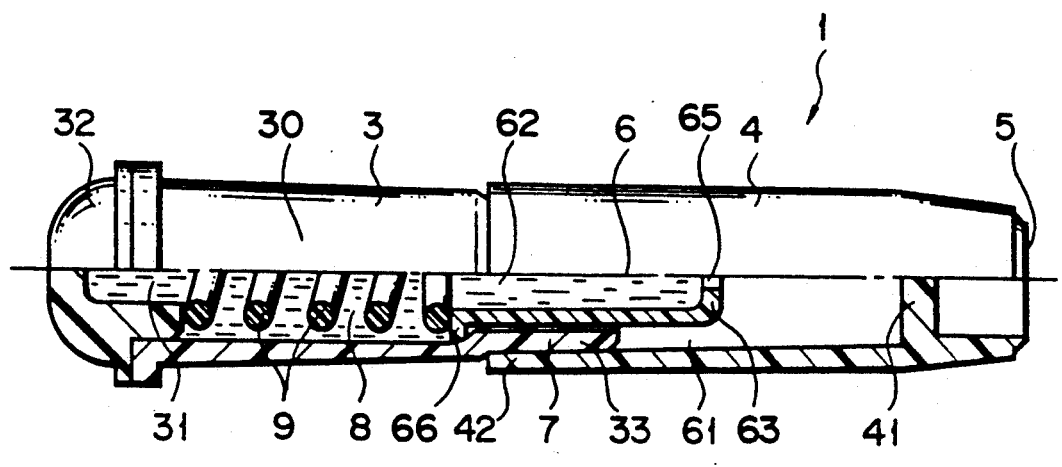
FIG. 6 is a sectional view explaining the application of the viscous liquid applicator after it is unsealed.

In the embodiment shown in FIG. 1, the coil spring 9 is not integral with the bottom cap 32. However, it may be preferably formed to be integral with the bottom cap 32, thereby reducing the number of components constituting the applicator 1. In this case, the spring 9 and the bottom cap 32 can be made of either the same material or two different materials Preferably, the liquid applicator 1 is a disposable one, which is thrown away after being used once or a few times. If the applicator 1 is of the type to be thrown away after being used a few times, the applying member 6 should not be left exposed between uses, so that it may not become contaminated and so that the applying material may not evaporate. This is why the distal open end portion 42 of the cap 4 is so shaped and sized as to hold, preferably in airtight fashion, the supporting portion 33 of the main body 3 as is shown in FIG. 6.

The present invention is not limited to the viscous liquid applicator shown in FIGS. 1 to 6. Rather, various changes and modifications can be made. For instance, the container 2 may comprise a main body and a cap fitted at one end in the main body or connected thereto in screw engagement. Further, the coil spring 9 can be dispensed with, and the applying member 6 may be made movable by securing same to the supporting portion 33 through a mechanical engagement device, as in the case of, for example, a lipstick, wherein the reciprocal movement of the applying member 6 can be realized through the rotation of the case portions.

The use of the liquid applicator according to the invention is not necessarily limited. The applicator can find uses in medical treatment, in offices, in food-processing, in cooking, and in manufacturing products.

According to the applicator of this invention, it has possible to coat viscous or semi-liquid materials with ease, and without requiring touching the tip of a finger to the applying material or applying portion, thereby avoiding a finger tip as well as the applying portion from being soiled or contaminated.

The shape of the cylindrical container 2 according to this invention is not limited to those having a circular cross-section, but may have a square cross-section or another polygonal cross-section.

Additional advantages and modifications will readily occur to those skilled in the art. Therefore, the invention in its broader aspects is not limited to the specific details, and representative devices, shown and described herein. Accordingly, various modifications may be made without departing from the spirit or scope of the general inventive concept as defined by the appended claims and their equivalents.

What is claimed is:

1. A viscous liquid applicator comprising:
    a cylindrical container having a closed bottom, said cylindrical container comprising an applying material-filling portion and a coater-supporting portion formed integral with a distal end portion of said applying material-filling portion;
    a viscous liquid applying material filled in said applying material-filling portion; and
    a cylindrical applying member having a barrier wall formed at and traversing a distal end portion thereof, and at least one through hole formed in said barrier wall for introducing air into said applying material-filling portion, said cylindrical applying member being slideably mounted in said coater-supporting portion so as to be reciprocally movable into and out of said cylindrical container, said cylindrical applying member being dimensioned relative to said coater-supporting portion so as to form a space between an outer wall of said cylindrical applying member and an inner wall of said coater-supporting portion for allowing said viscous liquid applying material to be extruded out of said applying material-filling portion, through said space, and to be coated on said outer wall of said cylindrical applying member when said cylindrical applying member is pushed into said applying material-filling portion to increase pressure in said applying material-filling portion to force said applying material out through said space.

2. A viscous liquid applicator according to claim 1, wherein said barrier wall is formed at an applying end portion of said cylindrical applying member.

3. A viscous liquid applicator according to claim 1, wherein said barrier wall is formed at an intermediate portion of said cylindrical applying member.

4. A viscous liquid applicator according to claim 1, wherein said applying material has a viscosity of 30 to 5000 cp at normal ambient temperature.

5. A viscous liquid applicator according to claim 1, wherein said applying material has a viscosity of 1000 to 3500 cp at normal ambient temperature.

6. A viscous liquid applicator according to claim 1, wherein said applying member comprises at least one groove on the circumferences thereof, said at least one groove extending along the length of the applying member.

7. A viscous liquid applicator according to claim 1, wherein further comprising an elastic member disposed in said applying material-filling portion to bias said applying ember in a direction opposite to said applying material-filling portion.

8. A viscous liquid applicator according to claim 7, wherein said elastic member comprises a coil spring.

9. A viscous liquid applicator according to claim 1, further comprising:
    a cap covering at least a portion of said applying member, and connected via a thin-walled breakable portion to said coater-supporting portion;
    one end of said cap which is disposed opposite to said thin-walled breakable portion being formed into a shape capable of capping said coater-supporting portion.

* * * * *